US011366239B2

(12) United States Patent
Lu et al.

(10) Patent No.: US 11,366,239 B2
(45) Date of Patent: Jun. 21, 2022

(54) HYBRID DOSIMETRY AND IMAGING SYSTEM

(71) Applicant: Varex Imaging Corporation, Salt Lake City, UT (US)

(72) Inventors: Minghui Lu, Fremont, CA (US); Joachim Steiger, New Boston, NH (US); Richard Aufrichtig, Palo Alto, CA (US)

(73) Assignee: Varex Imaging Corporation, Salt Lake City, UT (US)

( * ) Notice: Subject to any disclaimer, the term of this patent is extended or adjusted under 35 U.S.C. 154(b) by 63 days.

(21) Appl. No.: 16/528,547

(22) Filed: Jul. 31, 2019

(65) Prior Publication Data

US 2020/0041662 A1 Feb. 6, 2020

Related U.S. Application Data

(60) Provisional application No. 62/713,415, filed on Aug. 1, 2018.

(51) Int. Cl.
*A61N 5/10* (2006.01)
*G01T 1/20* (2006.01)
(Continued)

(52) U.S. Cl.
CPC .............. *G01T 1/2018* (2013.01); *A61N 5/10* (2013.01); *A61N 5/1048* (2013.01);
(Continued)

(58) Field of Classification Search
CPC .......... A61N 2005/1054; A61N 5/1048; A61N 5/1049; A61N 2005/1061; A61N 5/1071;
(Continued)

(56) References Cited

U.S. PATENT DOCUMENTS 6,791,090 B2 * 9/2004 Lin ......................... G01T 1/242
250/336.1
6,842,502 B2 * 1/2005 Jaffray ................... A61B 6/466
378/65
(Continued)

OTHER PUBLICATIONS

Blake, Samuel J., Characterization of a novel EPID designed for simultaneous imaging and dose verification in radiotherapy, Med. Phys. 40(9), Sep. 2013.
(Continued)

*Primary Examiner* — Allen C. Ho
(74) *Attorney, Agent, or Firm* — Laurence & Phillips IP Law (57) ABSTRACT

Some embodiments include a system, comprising a hybrid imaging device comprising: a first scintillator; a first detector sensors configured to generate a signal based on photons emitted from the first scintillator; a second scintillator; a second detector sensors configured to generate a signal based on photons emitted from the second scintillator; and a control logic coupled to the first detector layer and the second detector layer; wherein: a material of the first scintillator is different from a material of the second scintillator; the first detector overlaps the second detector; and the control logic is configured to generate dose data in response to the first detector and image data in response to the second detector.

20 Claims, 6 Drawing Sheets

(51) Int. Cl.
   *G01T 1/164* (2006.01)
   *G01T 1/208* (2006.01)
   *G01T 1/166* (2006.01)

(52) U.S. Cl.
   CPC ......... *A61N 5/1049* (2013.01); *A61N 5/1071* (2013.01); *G01T 1/1645* (2013.01); *G01T 1/1663* (2013.01); *G01T 1/20* (2013.01); *G01T 1/2006* (2013.01); *G01T 1/208* (2013.01); *G01T 1/2008* (2013.01); *G01T 1/20181* (2020.05); *G01T 1/20185* (2020.05); *A61N 2005/1054* (2013.01); *A61N 2005/1061* (2013.01)

(58) Field of Classification Search
   CPC ....... G01T 1/20; G01T 1/2006; G01T 1/2008; G01T 1/2018; G01T 1/20185
   USPC ............... 378/19, 98.8, 65, 98.9; 250/370.09
   See application file for complete search history.

(56) References Cited

U.S. PATENT DOCUMENTS

| | | | | |
|---|---|---|---|---|
| 6,888,919 | B2* | 5/2005 | Graf | A61N 5/1049 378/197 |
| 7,227,925 | B1* | 6/2007 | Mansfield | A61N 5/1049 378/41 |
| 7,263,165 | B2* | 8/2007 | Ghelmansarai | A61N 5/1049 250/370.09 |
| 7,412,024 | B1* | 8/2008 | Yun | A61B 6/484 378/53 |
| 7,671,342 | B2* | 3/2010 | Bani-Hashemi | G01T 1/2018 250/370.11 |
| 7,804,936 | B2* | 9/2010 | Pouliot | A61B 6/5282 378/65 |
| 7,848,488 | B2* | 12/2010 | Mansfield | A61N 5/1082 378/65 |
| 7,945,021 | B2* | 5/2011 | Shapiro | A61N 5/1049 378/65 |
| 8,173,969 | B2* | 5/2012 | Nishino | G03B 42/04 250/370.08 |
| 8,389,941 | B2* | 3/2013 | Bendahan | G01T 1/16 250/363.02 |
| 8,440,978 | B2 | 5/2013 | Morf | |
| 8,670,523 | B2* | 3/2014 | Yan | A61N 5/107 378/65 |
| 9,201,149 | B2* | 12/2015 | Ben Hayun | G01T 1/2018 |
| 9,244,178 | B2* | 1/2016 | Jung | G01T 1/2006 |
| 9,265,971 | B2* | 2/2016 | Baltes | A61B 6/52 |
| 9,268,037 | B2* | 2/2016 | Partain | G01T 1/20 |
| 9,526,466 | B2 | 12/2016 | Karim | |
| 9,616,251 | B2* | 4/2017 | Filiberti | A61N 5/1081 |
| 9,958,402 | B2* | 5/2018 | Ebstein | G01N 23/04 |
| 10,444,378 | B1* | 10/2019 | Mort | G01T 1/242 |
| 10,556,130 | B2* | 2/2020 | Dolney | A61N 5/1075 |
| 10,775,517 | B2* | 9/2020 | Maolinbay | A61N 5/1049 |
| 11,156,727 | B2* | 10/2021 | Shedlock | G01T 1/2018 |
| 2010/0252742 | A1 | 10/2010 | Tkaczyk | |
| 2013/0287170 | A1 | 10/2013 | Ebstein | |
| 2014/0353513 | A1 | 12/2014 | Partain | |
| 2016/0070003 | A1 | 3/2016 | Haiun | |
| 2017/0097425 | A1 | 4/2017 | Shedlock | |
| 2019/0038918 | A1 | 2/2019 | Lu | |

OTHER PUBLICATIONS

Blake, Samuel J., A high DQE water-equivalent EPID employing an array of plastic-scintillating fibers for simultaneous imaging and dosimetry in radiotherapy, Med. Phys. 45(5), May 2018.

Beddart A. S., Water-equivalent plastic scintillation detectors for high energy beam dosimetry: I. Physical characteristics and theoretical considerations, Phys. Med. Biol., vol. 37, No. 10, 1992.

Chen, Haijian, Super-resolution imaging in a multiple layer EPID, Biomed Phys Eng Express, Apr. 2018.

Rottmann, Joerg, A novel EPID design for enhanced contrast and detective quantum efficiency, Phys. Med. Biol., vol. 61, No. 17, 2016.

Vial, Phillip, Initial evaluation of a commercial EPID modified to a novel direct-detection configuration for radiotherapy dosimetry, Med. Phys. 35(10), Oct. 2008.

Yamane, T., Investigation of Flat Panel Detector Performance Using Various Scintillators in Neutron Imaging, Conference Presentation in Japan, 2014.

PCT/US2019/049376, International Search Report dated Jan. 22, 2020.

PCT/US2019/049376, Written Opinion dated Jan. 22, 2020.

PCT/US2019/049376, International Preliminary Reporton Patentability dated Feb. 2, 2021.

* cited by examiner

HYBRID DOSIMETRY AND IMAGING SYSTEM

Imaging devices such as an electronic portal imaging device (EPID) are used with medical linear accelerators as part of image guided radiotherapy. An EPID may be used in imaging bony structures and/or fiducial markers in treatment field verification. EPIDs include scintillators to convert the high energy X-ray from a linear accelerator into optical photons that can be detected by a photodetector.

DETAILED DESCRIPTION

Embodiments will be described where a hybrid imaging system includes at least two detector sub-systems. In some embodiments, one detector sub-system may be used to generate dose data for dosimetry applications while the other detector sub-system may be used to generate imaging data. Each of the detector sub-systems may include a different scintillator depending on the particular use.

Figure 1:
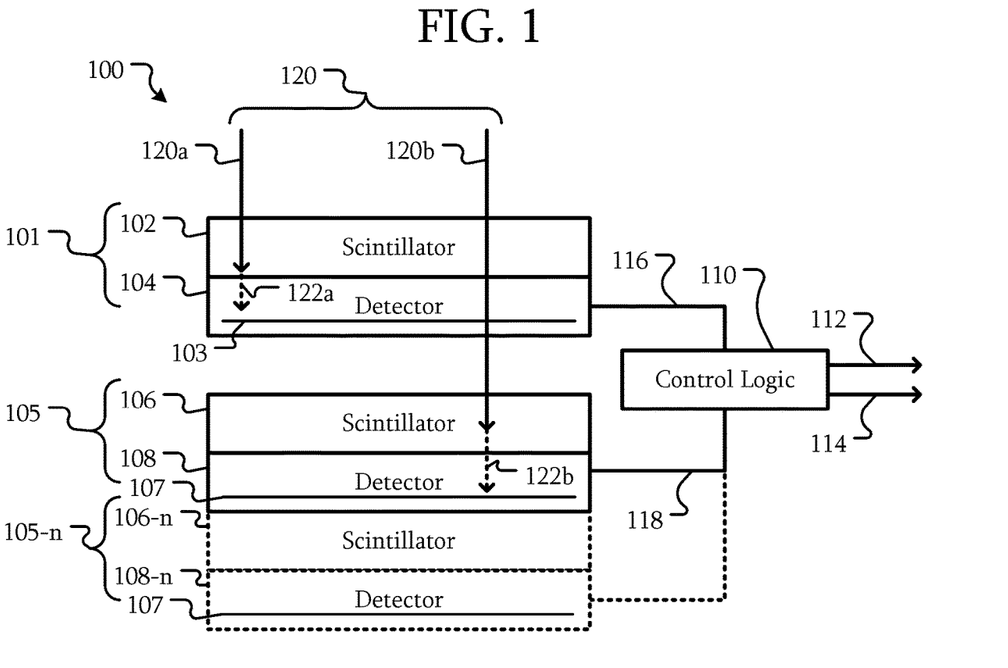
FIGS. 1-3 are block diagrams of systems with dosimetry and imaging sub-systems according to some embodiments.
Figure 2:
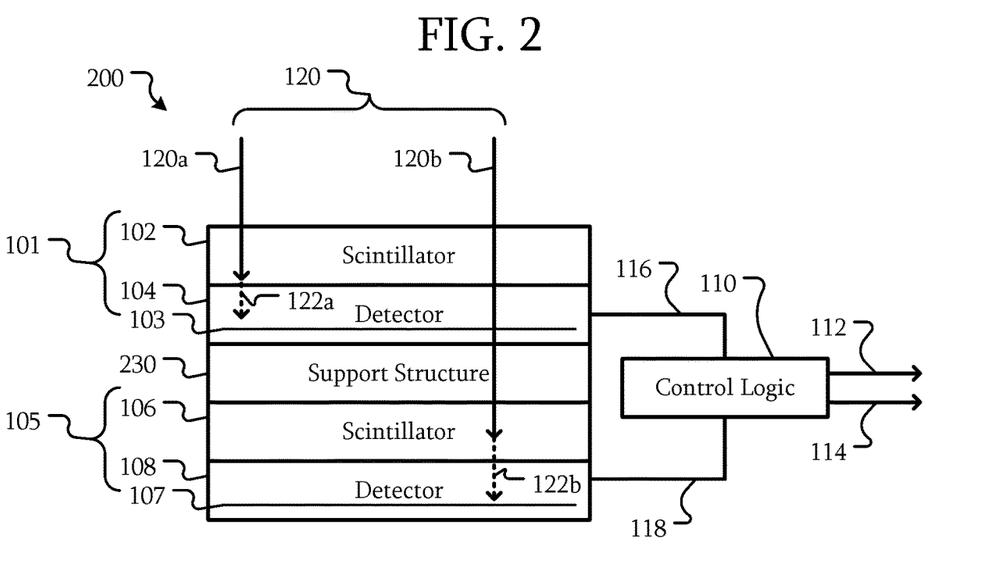
Figure 3:
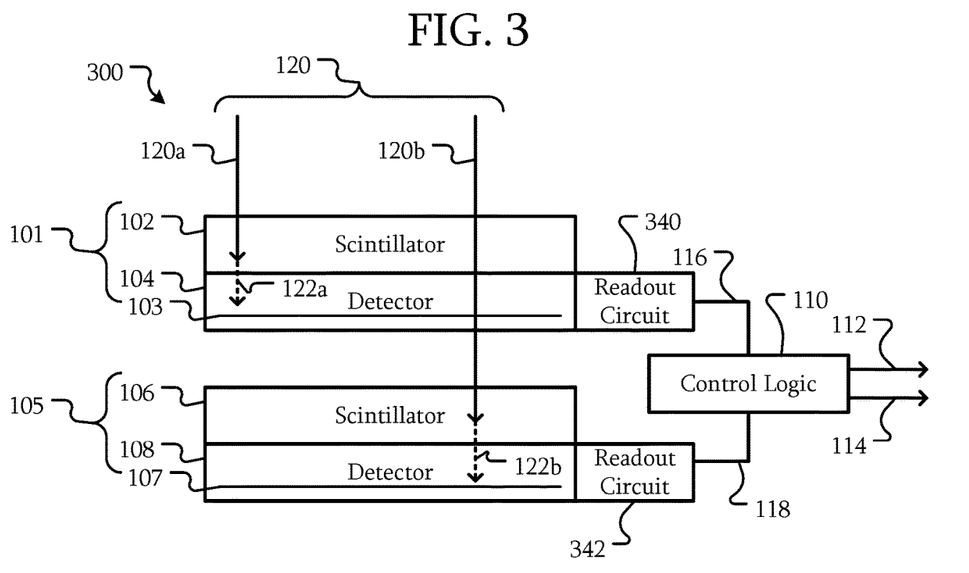

FIGS. 1-3 are block diagrams of systems with dose and imaging sub-systems according to some embodiments. Referring to FIG. 1, in some embodiments, a system 100 includes two overlapping detector sub-systems 101 and 105. The detector sub-systems 101 and 105 are coupled to control logic 110.

Detector sub-system 101 includes a scintillator 102 and a detector 104. The scintillator 102 includes a material that converts incoming photons 120a into photons 122a. For example, the photons 120a may include photons of a radiation beam 120, such as a megavolt (MV) x-ray beam. The scintillator 102 may convert the photons 120a into optical photons 122a, such as those in wavelengths from infrared to ultraviolet, including visible light. Although a particular wavelength range, voltage, and/or energy level has been used as an example, in other embodiments, the photons 120a and the converted photons 122a may have different characteristics.

In some embodiments, the material of the scintillator 102 includes a water-equivalent material. A water-equivalent material may include a material that has a mass energy-absorption coefficient that is similar to water over a target energy range for the incoming photons 120a. For example, a water-equivalent material may have a mass energy-absorption coefficient that is within about 15% or less of that of water over an energy range from about 0.1 megaelectronvolt (MeV) to 10 MeV. A non-water-equivalent material may have a mass energy-absorption coefficient that is greater than 15% of that of water over an energy range from about 0.1 MeV to 10 MeV. In other embodiments, the energy range over which a material is water-equivalent or non-water-equivalent may be different. Examples of water-equivalent material includes polymers, plastics, polymethylmethacrylate (PMMA), polystyrene, or the like.

The detector 104 is configured to generate a signal 116 in response to the photons 122a emitted from the scintillator 102. The detector 104 may have a plurality of pixels 103, each of which may be configured to convert one or more photons 122a into the signal 116. The pixels 103 of the detector 104 may include sensors such as photodetectors, photodiodes, phototransistors, or the like configured to generate a signal base on the incoming photons 122a. The detector 104 may include a variety of architectures. For example, the detector 104 may include an amorphous silicon (a-Si) detector, a complementary metal-oxide semiconductor (CMOS) detector, an amorphous indium-gallium-zinc-oxide (IGZO or GIZO) detector, or the like.

The signal 116 may take a variety of forms. In some embodiments, the signal 116 is the raw output from pixels of the detector 104. In other embodiments, the signal 116 may represent a signal integrated over time based on the photons 122a. Other processing may be performed by the detector 104 to generate the signal 116. Such operations may be performed by circuitry within the detector 104 such as integrators, photon counters, analog to digital converters, sample and hold circuits, memory, or the like.

The system 100 may include one or more detector sub-systems 105. The detector sub-system 105 includes a scintillator 106 and a detector 108. The scintillator 106 includes a material that converts incoming photons 120b into photons 122b. For example, the photons 120b may include photons of a radiation beam 120, such as an MV x-ray beam. The scintillator 106 may convert the MV photons 120b into optical photons 122b, such as those in wavelengths from infrared to ultraviolet, including visible light. Although a particular wavelength range and/or energy level has been used as an example, in other embodiments, the photons 120b and the converted photons 122b may have different characteristics. Moreover, the wavelength range and/or energy level of the photons 122b may be similar to different from that of the photons 122a.

The scintillator 106 may be formed of a variety of materials. For example, the scintillator 106 may include gadolinium oxysulfide ($Gd_2O_2S$; GOS; Gadox), gadolinium oxysulfide doped with terbium ($Gd_2O_2S$:Tb), cesium iodide (CsI), or the like. Although some materials of the scintillator 106 have been used as examples, in other embodiments, the material may be different depending on the particular system 100. In some embodiments, the material of the scintillator 106 is not a water-equivalent material or a non-water-equivalent material. For example, the material of the scintillator 106 may be selected to optimize a detective quantum efficiency (DQE).

In some embodiments, the scintillator 106 may include one or more additional layers. Examples of such additional layers include a copper (Cu) layer. The one or more additional layers may provide buildup, reduce saturation of pixels of the detector 108 for high energy radiation beams. However, in other embodiments, some additional layers may be omitted. For example, omitting such a copper layer may improve the sensitivity of the detector sub-system 105. In addition, the thickness of the scintillator 106 may be optimized for imaging purposes in some embodiments.

In some embodiments, the detector sub-system 101 overlaps the detector sub-system 105. As a result, an x-ray beam 120 including the photons 120a and 120b may pass through the scintillator 102 before passing through the scintillator 106.

The detector 108 is configured to generate a signal 118 in response to the photons 122b emitted from the scintillator 106. The detector 108 may have a plurality of pixels 107, each of which may be configured to convert one or more photons 122b into the signal 118. Similar to the signal 116, the signal 118 may take a variety of forms. However, the form of the signal 118, the information represented by the signal 118, or the like may be different than that of the signal 116. In some embodiments, the signal 116 may represent data that may be converted into dose information, or both dose and image information, while the signal 118 represents data that may be converted into an image.

The detector sub-systems 101 and 105 are coupled to control logic 110. The control logic 110 may include a processor such as a general purpose processor, a digital signal processor (DSP), an application specific integrated circuit, a microcontroller, a programmable logic device (e.g., field-programmable gate array [FPGA]), discrete circuits, a combination of such devices, or the like. The processor may include circuitry such as registers, cache memory, processing cores, or the like, and may also include external interfaces, such as address and data bus interfaces, interrupt interfaces, or the like. The control logic 110 may also include other interface devices, such as logic chipsets, hubs, memory controllers, communication interfaces, or the like that may be part of the system 100 to connect the processor to internal and external components.

The control logic 110 is configured to generate dose data 112 or both dose data 112 and image data 114 in response to the first detector 104 and image data 114 in response to the second detector 108. The dose data 112 may include information related to a delivered dose, dose rate, or the like. In some embodiments, the control logic 110 may receive the signal 116 and process that signal 116 into the dose data 112 and in some embodiments into the dose data 112 and at least part of the image data 114. The control logic 110 may receive the signal 118 and process that signal 118 and potentially the signal 116 into the image data 114 The image data 114 may include information related to the position of objects, information about the treatment field, or the like as represented by the beam 120.

In some embodiments, a material of the scintillator 102 is different from a material of the scintillator 106. For example, the scintillator 102 may include a water-equivalent material, such as PMMA, while the scintillator 106 may include a material that is not water-equivalent, such as GOS. The difference in the materials may allow the different detector sub-systems 101 and 105 to perform different functions. The detector sub-system 105 may be optimized to have a higher DQE for better imaging performance. In contrast, the detector sub-system 101 may have a lower DQE, but a better water-equivalence to improve an accuracy of measuring dose. For example, the DQE of the first scintillator 102 may be less than 2%, such as about 1%, while the DQE of the scintillator 106 may be higher than 2%. In some embodiments, a ratio of the DQE of the scintillator 102 to the DQE of the scintillator 106 may be 1:100 or less.

In some embodiments, a thickness of the material of the scintillator 102 may be less than 25 millimeters (mm). In some embodiments, the thickness may be less than 10 mm or less than 2 mm. In a specific example, the scintillator 102 may be a 5 mm thick sheet of PMMA. With MV x-ray beams, a thinner scintillator 102 may be acceptable. The lower DQE may reduce or eliminate a chance of pixels of the detector 104 saturating but may reduce the detector's sensitivity. In particular, with high dose rate or integrated dose rate applications, detector saturation may be an issue due to a higher DQE. The lower DQE allows for higher dose rates or integrated doses before saturation. In some embodiments, the scintillator 102 does not have a pixel structure. That is, the material of the scintillator 102 may be substantially continuous, homogenous, and/or laminar without divisions associated with pixels of the detector 104 forming homogenous and/or laminar layer. However, due to the lower thickness, divergence of the photons 122a may have less of an effect.

In some embodiments, a lag from the detector sub-system 101 with the scintillator 102 may be less than that of a lag from the detector sub-system 105 with the scintillator 106. For example, the detector with scintillator 106 may have a lag of about 3% when GOS is used as a scintillating material. However, when a plastic or polymer is used for the scintillator 102, the lag may be zero, negligible, or the like. The lower lag may result in more accurate field verification for high dose rate treatments.

As described above, the system 100 may include one or more detector sub-systems 105. In particular, some embodiments may include two or more detector sub-systems 105. While one additional detector sub-system 105 has been used as an example for the system 100, in other embodiments a different number of additional detector sub-systems 105. For example, n detector sub-systems 105 may be part of the system 100 as represented by detector sub-systems 105 to 105-n. In some embodiments, the detector sub-systems 105 may be similar, but in other embodiments, the detector sub-systems 105 may be different. For example, multiple detector sub-systems 105 may be present, each with a different scintillator 106 type and/or material and/or pixel alignment between different sub-systems 105. In other figures embodiments of systems may include multiple detector sub-systems 105; however, those additional detector sub-systems 105 will not be illustrated for clarity.

Although embodiments where the incoming beam 120 is a beam of photons, in other embodiments, the incoming beam 120 may include other particles. For example, the incoming beam 120 may be a neutron beam. The scintillators 102 and 106 may include materials that convert at least some neutrons into the photons 122a and 122b. Examples of such materials include lithium (Li), lithium-6-fluoride ($^6$LiF), zinc sulfide phosphor (ZnS:Ag), or the like. Although neutrons have been used as an example, in other embodiments, other charged particles may form the beam 120 and the scintillators 102 and 106 may be selected to convert those particles into photons 122a and 122b detectable by the detectors 104 and 108.

Referring to FIG. 2, in some embodiments, the system 200 is similar to system 100 of FIG. 1. The system 200 includes a support structure 230. In some embodiments, the support structure 230 is disposed between the detector sub-systems 101 and 105. However, in other embodiments, the support structure 230 may be disposed in other location, such as on a side with the scintillator 102 or on a side with the detector 108. The support structure may be a material that is substantially transparent to the photons 120a and/or 120b.

In some embodiments, the support structure 230 may include a material that filters particles that may reach the scintillator 106. For example, the support structure 230 may include a material, such as copper, to provide buildup to reduce saturation of pixels of the detector 108 for high energy radiation beams. For example, the support structure 230 may include a material that may block thermal neutrons, such as boron rich materials. As a result, particles reaching the scintillator 106 may include only photons or a greater proportion of photons. As a material of the scintillator 106 may interact with both neutrons and photons, reducing or eliminating the incident neutrons may allow for analyzing the source contributions from photons or neutrons, analyze photon contamination of a neutron source, or the like.

In some embodiments, obtaining both neutron and photon information allows for complimentary sets of data as photons and neutrons are affected in a complimentary manner by various materials. For example, x-ray photons may be stopped more by high atomic number materials such as lead, nickel, iron, or the like. In contrast, neutrons may be stopped more by lower atomic number materials such as hydrogen, boron, or the like.

Referring to FIG. 3, the system 300 may be similar to the systems 100 and 200 of FIGS. 1 and 2. The detectors 104 and 108 are coupled to readout circuits 340 and 342, respectively. The readout circuits 340 and 342 may include circuitry such as row and column circuits, sampling circuits, analog to digital converters, memory, buffers, or the like configured to convert signals received by pixels of the detectors 104 and 108 into the signals 116 and 118, respectively.

In some embodiments, the readout circuits 340 and 342 may be independently operated. For example, as described above, the detector sub-system 101 may be used to generate dose data 112 while the detector sub-system 105 may be used to generate image data 114. The acquisition periods, acquisition techniques, or the like may be different such as being different to optimize the generation of either dose data 112 or image data 114.

Figure 4A:
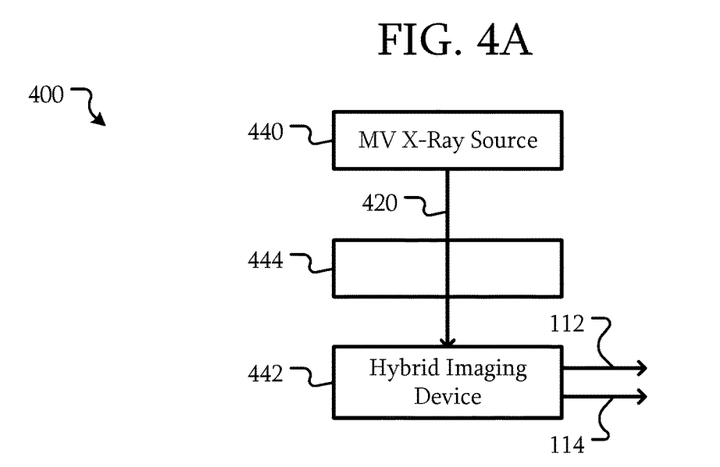
FIGS. 4A and 4B are block diagrams of x-ray systems according to some embodiments.
Figure 4B:
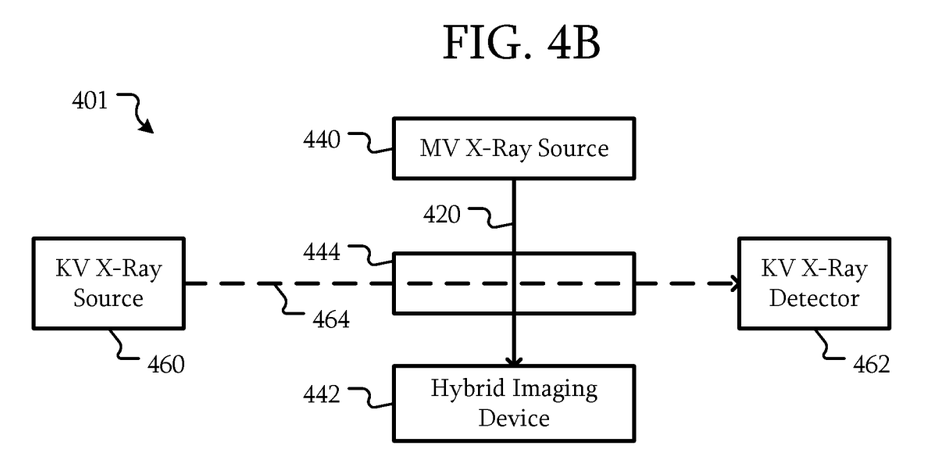

FIGS. 4A and 4B are block diagrams of x-ray systems according to some embodiments. Referring to FIG. 4A, in some embodiments, a system 400 includes an MV x-ray source 440 configured to generate an x-ray beam having photons with energies greater than 1 MeV. The MV x-ray source 440 may include devices such as a linear accelerator or other similar devices. In a particular example, the MV x-ray source 440 may be configured to generate a 6 MV flattened beam with a dose rate of about 550 to about 600 monitor units (MU) per minute.

The system 400 also includes a hybrid imaging device 442. The hybrid imaging device 442 may include a system described herein such as systems 100, 200, 300, or the like. For example, the x-ray beam 420 may include the photons 120a and 120b or the like as described above. The hybrid imaging device 442 is disposed to be in the path of the x-ray beam 420. For example, the MV x-ray source 440 may be mounted on a rotatable gantry (not illustrated). The hybrid imaging device 442 may be referred to as a hybrid dosimetry and imaging detector, a hybrid radiation detector, a dual-layer radiation detector, a multi-layered radiation detector, a hybrid EPID, a dual-layer EPID, or multi-layered EPID. In some embodiments, components of the hybrid imaging device 442 are at least partial enclosed in a housing or case. The device housing can include metal, such as aluminum or the like, or polymers, such as carbon fiber, or the like.

The system 400 may be used for a variety of applications. Examples of such applications include radiotherapy, non-destructive testing, or the like. In a particular example, in some embodiments, the hybrid imaging device 442 may be used for radiotherapy for non-transmission pre-treatment verification, non-transmission treatment verification of a specimen or patient 444 such as positioning before treatment, transmission dosimetry before and/or during treatment, or the like. In a particular example, the system 400 described herein may be used for simultaneous/real-time dosimetry and imaging of an MV cancer treatment beam. In another example, the detector sub-system 105 of the hybrid imaging device 442 may be used in imaging bony structures, fiducial markers, or the like. In addition, the detector sub-system 105 may be used for patient positioning, marker tracking, treatment field verification. The detector sub-system 101 may be used for dosimetry applications such as dose measurement for patient quality assurance before treatment delivery, for dose delivery verification during treatment, or the like.

Scintillating materials such as GOS may not be water-equivalent for MeV photons. As a result, using a detector with such materials may not be as accurate a dosimetry tool for patient quality assurance (QA) and in-vivo treatment dosimetry verification. By using a detector sub-system 101 having a water-equivalent scintillator 102 as described herein, dosimetry applications may be improved while maintaining the performance for imaging applications. In a specific example, the plastic water-equivalent scintillator 102 allows for more accurate dose measurements while using GOS for the scintillator 106 allows for imaging capabilities.

Referring to FIG. 4B, in some embodiments, the system 401 may be similar to the system 400 of FIG. 4A. However, the system 401 includes a kilovolt (KV) x-ray source 460 and a KV detector 462. The KV x-ray source 460 may include an x-ray tube or other similar structures. The KV detector 462 is a detector configured to detect particles having energies in the kiloelectronvolt (keV) ranges, such as photons with energies less than 1 MeV. In some embodiments, the KV detector 462 may include a flat panel detector.

In some embodiments, the MV x-ray source 440 and the KV x-ray source 460 may be mounted on the same structure, such as the rotatable gantry, ring structure, c-arm, or the like. However, in other embodiments, the MV x-ray source 440 and the KV x-ray source 460 may be mounted independently.

In some embodiments, the MV x-ray source 440 and the KV x-ray source 460 may be configured to generate orthogonal x-ray beams 420 and 464. As a result, two orthogonal images may be used for patient positioning or other operations.

In some embodiments, the system 401 may be operated as a radiotherapy system. The specimen or patient 444 may be disposed on a couch or other support structure. The flow for the system 401 may be similar to that of a conventional radiotherapy system. However, the use of a hybrid imaging device 442 allows for additional dose data to be generated before and/or during a treatment and/or other operations.

Figure 5:
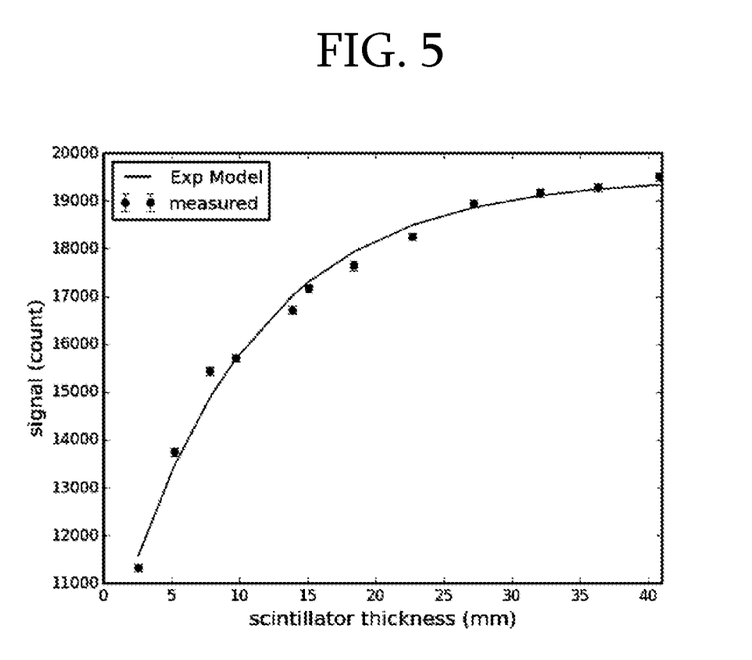
FIG. 5 is a chart of a detected signal versus plastic scintillator thickness according to some embodiments.

FIG. 5 is a chart of a detected signal versus plastic scintillator thickness according to some embodiments. The detector 104 response of different plastic scintillator 102 thickness may be modelled by an exponential function in Equation 1.

$$S = a \cdot (1 - e^{-(t-b) \cdot c}) \qquad \text{Equation 1}$$

Here, S is the detector signal, t is the scintillator thickness. The detector signal S may represent an Analog-to-Digital Unit (ADU), a photon count, an intensity value, or the like. This value may be expressed in integer units. The detector response at any scintillator thickness can be derived from the fitted model for the particular MV beam. Variables a, b, and c represent values determined experimentally.

Figure 6A:
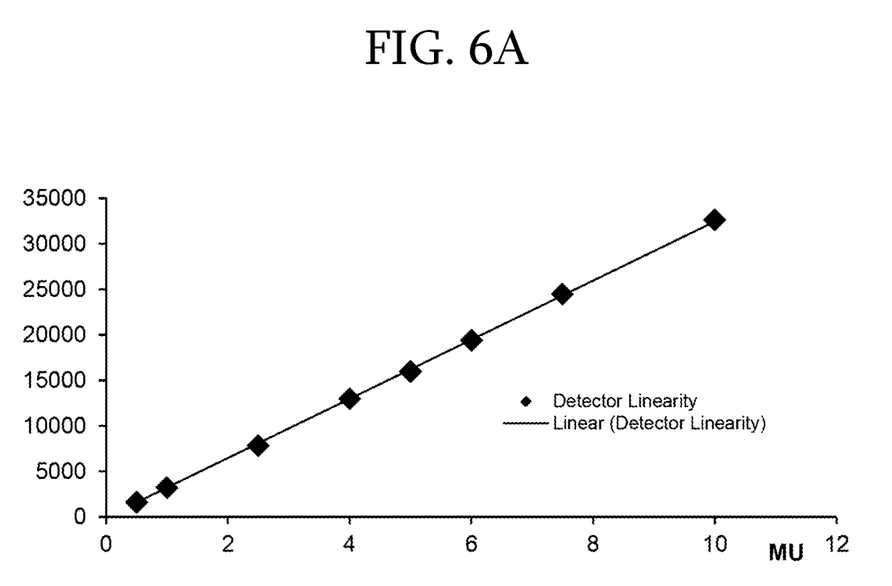
FIG. 6A is a graph of detector signal versus delivered dose according to some embodiments.
Figure 6B:
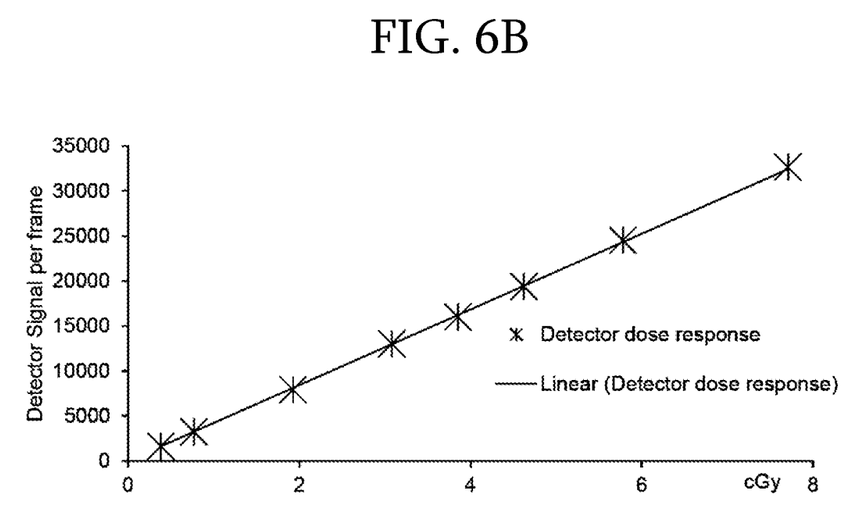
FIG. 6B is a graph of detector signal versus absorbed dose according to some embodiments.

FIG. 6A is a graph of detector signal versus delivered dose in monitor units (MU) for 5.2 mm thick plastic scintillator according to some embodiments. FIG. 6B is a graph of detector signal versus absorbed dose for the same scintillator thickness according to some embodiments. Referring to FIGS. 6A and 6B, in some embodiments, the detector signal may be calibrated to absolute dose by ion chamber measurement. For example, an absorbed dose can be measured by an ion chamber at the same water depth as the scintillator thickness, i.e., 5.2 mm. That measurement may be used to convert the delivered dose of FIG. 6A into the absolute dose of FIG. 6B for the same scintillator thickness. In some embodiments, the detector signal can be calibrated to absolute dose measurement with a single ion chamber measurement. The dose calibration curve for other scintillator thickness (thus different water depth) can be derived from the fitted model of Equation 1. Although the use of a particular scintillator thickness of 5.2 mm has been used as an example, in other embodiments, different thicknesses of scintillators may be used.

Figure 7:
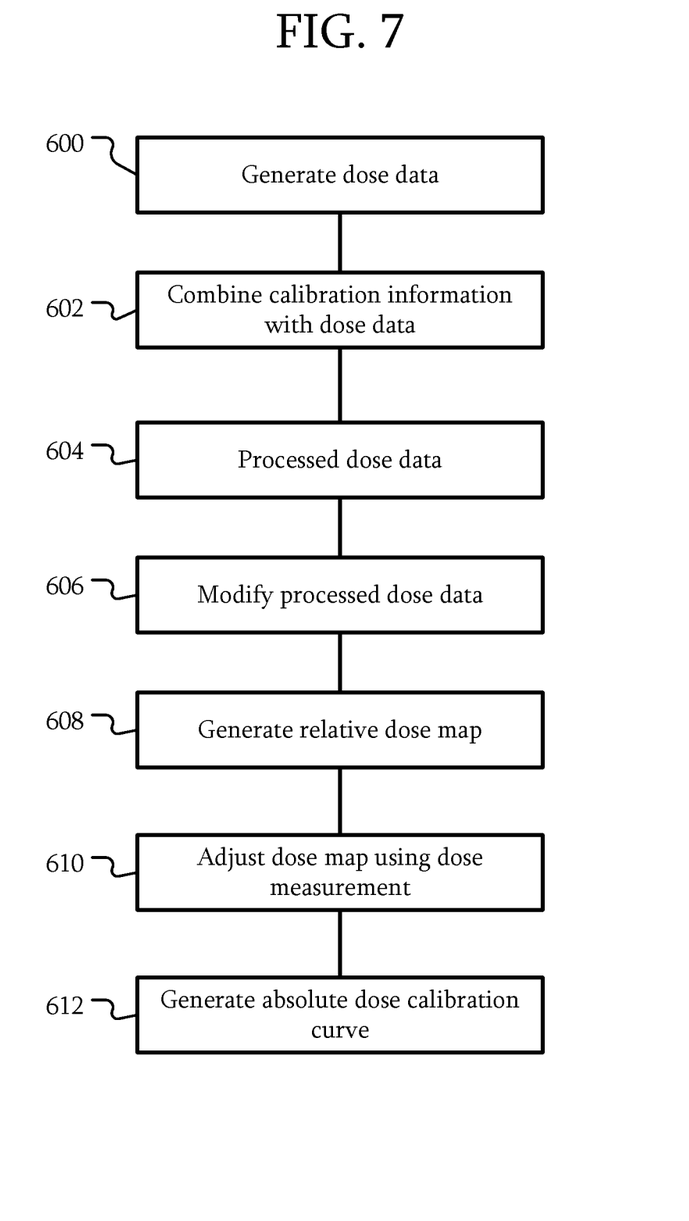
FIG. 7 is a flowchart of calibration of the dose according to some embodiments.

FIG. 7 is a flowchart of calibration of the dose according to some embodiments. A system 100 of FIG. 1 will be used as an example; however, the operations may be performed using other similar systems. In 600, dose data is generated in response to the detector sub-system 101. The dose data may be dose images of flattened beam square fields at a particular distance, such as 100 centimeters (cm) from the source. The dose data is combined in 602 with calibration information such as an open filed detector gain calibration, an offset correction, or the like resulting in processed dose data in 604.

In 606, the processed dose data is modified based on the water equivalence of the scintillator 102. In some embodiments, an off-axis beam correction may be applied. The result 608 is a relative dose distribution in water, or a relative dose map that is linear to the delivered dose.

In 610, the result 608 is processed with a dose measurement such as an ion chamber square field dose measurement at substantially the same depth as the scintillator 102. The result 612 is an absolute dose calibration curve describing a relationship between absorbed dose and pixel output. For example, the result 612 may represent a transformation of a pixel output to an absolute dose in grays (Gy) as illustrated in FIG. 6B for that water depth.

Although a 6 MV x-ray source 440 from a medical linac has been used as an example, in other embodiments, a source with a different mean energy may be used. For example, the source 440 may include a 10 MV flattened X-ray source, a 6 MV non-flattened X-ray source, or the like.

Figure 8:
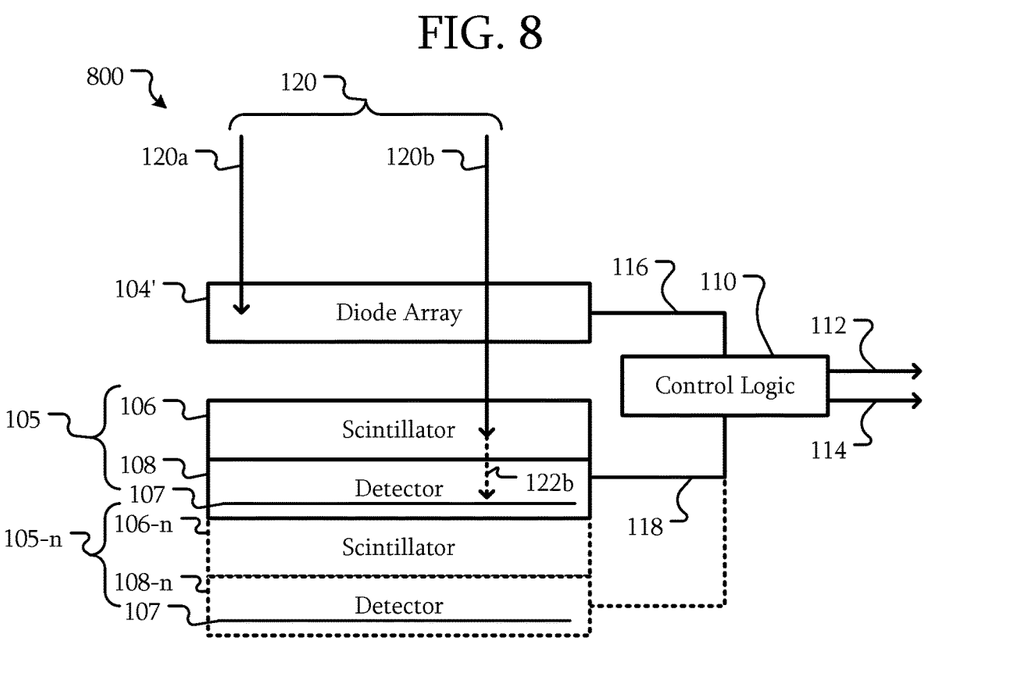
FIGS. 8 and 9 are block diagrams of systems with dosimetry and imaging sub-systems according to some embodiments.
Figure 9:
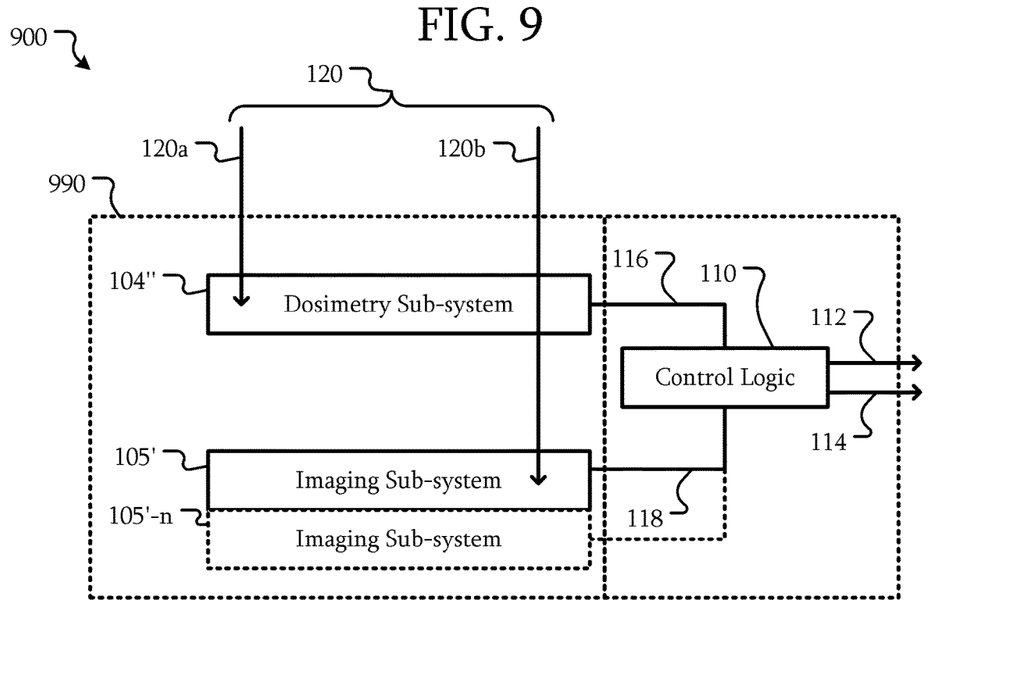

FIGS. 8 and 9 are block diagrams of systems with dosimetry and imaging sub-systems according to some embodiments. Referring to FIG. 8, the system 800 may be similar to the systems 100, 200, 300, or the like described above. However, the system 800 includes a diode array 104'. The diode array 104' is an array of diodes configured to directly detect the incoming x-ray photons 120a. The diode array 104' may operate in a manner similar to the detector sub-systems 101 described above. That is, the diode array 104' may be configured to generate the signal 116 that is then use to generate the dose data 112.

Referring to FIG. 9, the system 800 may be similar to the systems 100, 200, 30, 800, or the like described above. However, the system 800 includes a dosimetry sub-system 104" and one or more imaging sub-systems 105' to 105"-*n*. The dosimetry sub-system 104" may include the detector sub-systems 101, the diode array 104', ion chamber array, or the like as described above. The imaging sub-system 105" may include the detector sub-systems 105 described above.

In some embodiments, the dosimetry sub-system 104" and the imaging sub-systems 105' to 105'-*n* may be disposed in part or in full within a housing 990. In some embodiments, the control logic 110 may also be disposed in part or in full within the housing 990 as represented by the extended dashed lines. As described above, the housing 990 may include metal, such as aluminum or the like, or polymers, such as carbon fiber, or the like. Accordingly, in some embodiments, a single unit encompassed by the housing 990 may be configured to output both dose data 112 and image data 114.

Some embodiments include a system, comprising a hybrid imaging device comprising: a first scintillator 102; a first detector 104 sensors configured to generate a signal based on photons emitted from the first scintillator 102; a second scintillator 106; a second detector 108 sensors configured to generate a signal based on photons emitted from the second scintillator 106; and a control logic 110 coupled to the first detector 104 sensors and the second detector 108 sensors; wherein: a material of the first scintillator 102 is different from a material of the second scintillator 106; the first detector 104 sensors overlap the second detector 108 sensors; and the control logic 110 is configured to generate dose data in response to the first detector 104 and image data in response to the second detector 108.

In some embodiments, the material of the first scintillator 102 is a water-equivalent material.

In some embodiments, the material of the first scintillator 102 is a plastic.

In some embodiments, the material of the first scintillator 102 has a thickness of less than 10 millimeters (mm).

In some embodiments, the material of the second scintillator 106 is not a water-equivalent material.

In some embodiments, the material of the second scintillator 106 is gadolinium sulfoxylate.

In some embodiments, the hybrid imaging device further comprises a support structure 230 disposed between the first detector 104 and the second detector 108.

In some embodiments, the hybrid imaging device further comprises: a support structure 230 disposed between the first detector 104 and the second detector 108; wherein the support structure 230 includes a material configured to block neutrons.

In some embodiments, the first scintillator 102, the first detector 104, the second scintillator 106, the second detector 108, and the control logic 110 are enclosed in a housing 990.

In some embodiments, a detective quantum efficiency of the first scintillator 102 and the first detector 104 is less than 2%.

In some embodiments, the first scintillator 102 does not have a pixel structure.

In some embodiments, the first scintillator 102 has a homogenous and/or laminar structure In some embodiments, the hybrid imaging device further comprises a first readout circuit 340 coupled to the first detector 104; and a second readout circuit 342 coupled to the second detector 108.

In some embodiments, the system further comprises an x-ray source 440 configured to generate an x-ray beam with photons having an energy greater than 1 megaelectronvolt (MeV); wherein the first scintillator 102 is disposed such that the x-ray beam passes through the first scintillator 102 before passing through the second scintillator 106.

Some embodiments include a method, comprising: converting a part of incoming photons into first converted photons with a first scintillator 102; passing remaining photons of the incoming photons to a second scintillator 106; converting a part of the remaining photons into second converted photons with the second scintillator 106; generating dose data in response to the first converted photons; and generating image data in response to the second converted photons.

In some embodiments, a material of the first scintillator 102 is a water-equivalent material.

In some embodiments, the material of the first scintillator 102 is a polymer.

In some embodiments, a material of the second scintillator 106 is a non-water-equivalent material.

In some embodiments, the method further comprises generating an absolute dose calibration curve; wherein generating the dose data comprises generating the dose data in response to the absolute dose calibration curve.

In some embodiments, the material of the second scintillator 106 is gadolinium sulfoxylate.

In some embodiments, simultaneously generating the dose data in response to the first converted photons and generating the image data in response to the second converted photons.

In some embodiments, the incoming photons comprises an x-ray beam having an energy greater than 1 megavolt (MV).

Some embodiments include a system, comprising: means for converting a part of incoming photons into first converted photons and passing remaining photons of the incoming photons; means for converting a part of the remaining photons into second converted photons; means for generating dose data in response to the first converted photons; and means for generating image data in response to the second converted photons.

Examples of the means for converting a part of incoming photons into first converted photons and passing remaining photons of the incoming photons include, for example, the scintillator 102.

Examples of the means for converting a part of the remaining photons into second converted photons include, for example, the scintillator(s) 106.

Examples of the means for generating dose data in response to the first converted photons include, for example, the detector 104, the readout circuit 340, and the control logic 110.

Examples of the means for generating image data in response to the second converted photons include, for example, the detector(s) 108, the readout circuit 340, and the control logic 110.

In some embodiments, the system further comprises means for generating an x-ray beam including the incoming photons having an energy greater than 1 megaelectronvolt (MeV). Examples of the means for generating an x-ray beam including the incoming photons having an energy greater than 1 MeV include, for example, the MV x-ray source 440.

Although the structures, devices, methods, and systems have been described in accordance with particular embodiments, one of ordinary skill in the art will readily recognize that many variations to the particular embodiments are possible, and any variations should therefore be considered to be within the spirit and scope disclosed herein. Accordingly, many modifications may be made by one of ordinary skill in the art without departing from the scope of the appended claims.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the claims beginning with claim [x] and ending with the claim that immediately precedes this one," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed to cover the corresponding structure, material, or acts described herein and equivalents thereof in accordance with 35 U.S.C. § 112 ¶6. Embodiments of the invention in which an exclusive property or privilege is claimed are defined as follows.

The invention claimed is:

1. A system, comprising a hybrid imaging device comprising:
    a first scintillator;
    a first detector including first detector pixels configured to generate a signal based on photons emitted from the first scintillator;
    a second scintillator;
    a second detector including second detector pixels configured to generate a signal based on photons emitted from the second scintillator; and
    a control logic coupled to the first detector pixels and the second detector pixels;
    wherein:
        a material of the first scintillator is different from a material of the second scintillator;
        the first detector pixels overlap the second detector pixels; and
        the control logic is configured to generate dose data in response to the first detector and image data in response to the second detector.

2. The system of claim 1, wherein the material of the first scintillator comprises a water-equivalent material.

3. The system of claim 2, wherein the water-equivalent material comprises a polymer.

4. The system of claim 2, wherein the material of the first scintillator has a thickness of less than 10 millimeters (mm).

5. The system of claim 2, wherein the material of the second scintillator comprises a non-water-equivalent material.

6. The system of claim 1, wherein the hybrid imaging device further comprises:
    a support structure disposed between the first detector and the second detector.

7. The system of claim 1, further comprising:
    a housing;
    wherein the first scintillator, the first detector, the second scintillator, the second detector, and the control logic are enclosed in the housing.

8. The system of claim 1, wherein a detective quantum efficiency of the first scintillator and the first detector is less than 2%.

9. The system of claim 1, wherein the first scintillator comprises a homogenous and/or laminar structure.

10. The system of claim 1, wherein the hybrid imaging device further comprises:
a first readout circuit coupled to the first detector; and
a second readout circuit coupled to the second detector.

11. The system of claim 1, further comprising:
an x-ray source configured to generate an x-ray beam with photons having an energy greater than 1 megaelectronvolt (MeV);
wherein the first scintillator is disposed such that the x-ray beam passes through the first scintillator before passing through the second scintillator.

12. A method, comprising:
converting a part of incoming photons into first converted photons with a first scintillator;
passing remaining photons of the incoming photons to a second scintillator;
converting a part of the remaining photons into second converted photons with the second scintillator;
generating dose data in response to the first converted photons; and
generating image data in response to the second converted photons.

13. The method of claim 12, wherein a material of the first scintillator comprises a water-equivalent material.

14. The method of claim 13, wherein the water-equivalent material comprises a polymer.

15. The method of claim 12, wherein a material of the second scintillator comprises a non-water-equivalent material.

16. The method of claim 12, further comprising:
generating an absolute-dose calibration-curve;
wherein generating the dose data in response to the first converted photons comprises generating the dose data in response to the absolute-dose calibration-curve.

17. The method of claim 12, further comprising:
simultaneously generating the dose data in response to the first converted photons and generating the image data in response to the second converted photons.

18. The method of claim 12, wherein the incoming photons comprise an x-ray beam having an energy greater than 1 megaelectronvolt (MeV).

19. A system, comprising:
means for converting a part of incoming photons into first converted photons and passing remaining photons of the incoming photons;
means for converting a part of the remaining photons into second converted photons;
means for generating dose data in response to the first converted photons; and
means for generating image data in response to the second converted photons.

20. The system of claim 19, further comprising:
means for generating an x-ray beam including the incoming photons having an energy greater than 1 megaelectronvolt (MeV).

* * * * *